(12) United States Patent
Zamek et al.

(10) Patent No.: US 10,429,321 B2
(45) Date of Patent: Oct. 1, 2019

(54) APPARATUS FOR HIGH-SPEED IMAGING SENSOR DATA TRANSFER

(71) Applicant: KLA-Tencor Corporation, Milpitas, CA (US)

(72) Inventors: Steve Zamek, Sunnyvale, CA (US); David L. Brown, Los Gatos, CA (US); Venkatraman Iyer, Sunnyvale, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/671,729

(22) Filed: Aug. 8, 2017

(65) Prior Publication Data

US 2018/0059033 A1   Mar. 1, 2018

Related U.S. Application Data

(60) Provisional application No. 62/380,742, filed on Aug. 29, 2016.

(51) Int. Cl.
*G01N 21/95* (2006.01)
*G01T 1/24* (2006.01)
(Continued)

(52) U.S. Cl.
CPC .......... *G01N 21/9501* (2013.01); *G01T 1/24* (2013.01); *H01L 27/14618* (2013.01); *H01L 27/14636* (2013.01); *H04N 5/2256* (2013.01); *H04N 5/37206* (2013.01); *H01J 37/28* (2013.01); *H01J 2237/2441* (2013.01); *H01J 2237/2447* (2013.01); *H04N 5/372* (2013.01)

(58) Field of Classification Search
CPC .. G01N 21/9501; G01T 1/24; H01L 27/14618
See application file for complete search history.

(56) References Cited

U.S. PATENT DOCUMENTS 6,517,360 B1   2/2003  Cohen
7,081,373 B2   7/2006  Roeters et al.
(Continued)

FOREIGN PATENT DOCUMENTS

JP   2005079536 A   3/2005
JP   2005085976 A   3/2005
JP   2005101316 A   4/2005

*Primary Examiner* — Hugh Maupin
(74) *Attorney, Agent, or Firm* — Suiter Swantz pc llo

(57) ABSTRACT

An imaging sensor assembly includes at least one substrate including a plurality of substrate signal lines. The imaging sensor assembly also includes at least one imaging sensor package disposed on the at least one substrate, the at least one imaging sensor package including at least one imaging sensor disposed on at least one imaging sensor package substrate. The imaging sensor assembly also includes at least one receiver package disposed on the at least one substrate, the receiver package including at least one receiver integrated circuit disposed on at least one receiver package substrate. The imaging sensor assembly also includes at least one electrical interconnect operably coupled to the at least one imaging sensor package and the at least one receiver package. A plurality of data signals are transmitted between the at least one imaging sensor package and the at least one receiver package via the at least one electrical interconnect.

26 Claims, 8 Drawing Sheets

(51) Int. Cl.
   *H01L 27/146*   (2006.01)
   *H04N 5/372*    (2011.01)
   *H04N 5/225*    (2006.01)
   *H01J 37/28*    (2006.01)

(56) References Cited

U.S. PATENT DOCUMENTS

| | | |
|---|---|---|
| 7,148,428 B2 | 12/2006 | Meier et al. |
| 7,249,953 B2 | 7/2007 | Tutt |
| 7,609,309 B2 | 10/2009 | Brown et al. |
| 7,897,902 B2 | 3/2011 | Katzir et al. |
| 8,139,840 B1 | 3/2012 | Chu et al. |
| 8,231,284 B2 | 7/2012 | Doany et al. |
| 8,624,971 B2 | 1/2014 | Brown et al. |
| 8,711,575 B2 | 4/2014 | Lee |
| 8,748,828 B2 | 6/2014 | Brown et al. |
| 2005/0155223 A1 | 7/2005 | Fjelstad et al. |
| 2013/0176552 A1* | 7/2013 | Brown .............. H01L 27/14806 356/51 |
| 2013/0315528 A1 | 11/2013 | Levy |
| 2014/0268118 A1 | 9/2014 | Xu et al. |
| 2016/0064184 A1 | 3/2016 | Brown et al. |
| 2016/0234604 A1* | 8/2016 | Saxena ................. H04R 19/04 |

* cited by examiner

APPARATUS FOR HIGH-SPEED IMAGING SENSOR DATA TRANSFER

CROSS-REFERENCE TO RELATED APPLICATIONS

The present application claims the benefit under 35 U.S.C. § 119(e) of U.S. Provisional Patent Application Ser. No. 62/380,742, filed Aug. 29, 2016, entitled METHOD FOR DATA TRANSFER FROM A HIGH-SPEED SCANNING SENSOR, naming Steve Zamek, David L. Brown, and Venkatraman Iyer as inventors, which is incorporated herein by reference in the entirety.

TECHNICAL FIELD

The present invention generally relates to imaging sensors suitable for implementation in semiconductor inspection and metrology systems, and, more particularly, to high-speed imaging sensor data transfer in semiconductor inspection and metrology systems.

BACKGROUND

The demand for improved semiconductor device inspection and metrology systems continues to increase. Inspection systems, for example, typically include one or more imaging or scanning sensors, where the one or more imaging or scanning sensors are part of an integrated circuit package. The integrated circuit package may be mounted on a printed circuit board (PCB) or disposed on an interposer mounted on the PCB. High-speed image sensor imaging and scanning requires communication signal paths with controlled impedance, which may place fine design-rule requirements on the PCB.

If multiple integrated circuit packages are mounted directly or indirectly to the PCB, one or more signal lines coupling the integrated circuit packages together may be embedded within the PCB. The one or more signal lines may require high-speed communication channel signal drivers (e.g. optical transceivers). High-speed scanning and imaging sensors can generate a high total data rate, which is sustained for a selected period of inspection time. Although the signal drivers need to be robust, error-free, and capable of sustaining high-speed data rates, the extended sustaining of a high-speed data rate makes significant buffering of the data capturing and transmission difficult.

As imaging sensors are typically fabricated with dedicated integrated circuit packages, the signal drivers may include design constraints (e.g. power dissipation, temperature stability, spacing, and/or fabrication constraints) that limit the performance of the image sensor system and/or degrade the quality of the measurement signal. Additionally, the high density of signals necessary for the high-speed data transfer may place fine design-rule requirements on the PCB trace and/or connector design. As the number of design constraints on the PCB increases, the fabrication of the PCB layers and the assembly of the connectors become increasingly difficult and error-prone. Limitations on the PCB design, even if only a small region of the PCB, may limit the choice of PCB materials and/or increase the cost of the entire PCB.

Where an inspection or metrology system includes one or more arrays of sensors, the conventional approach utilizes either an array of small, modular PCBs or a single main PCB. A single main PCB includes a stable set of power supply and ground connections for all coupled devices, and additionally includes PCB control and logic in a single setup instead of a setup split apart onto multiple boards. Additionally, total component count to fabricate the single main PCB is typically lower than the total component count for an array of small, modular boards. However, a single main PCB is subjected to additional design constraints with high-speed data rates, making fabrication of the single main PCB more difficult and more expensive than an array of small, modular boards.

Therefore, it would be advantageous to provide a system that addresses the shortcomings described above.

SUMMARY

An imaging sensor assembly is disclosed, in accordance with one or more embodiments of the present disclosure. In one embodiment, the imaging sensor assembly includes at least one substrate. In another embodiment, the at least one substrate includes a plurality of substrate signal lines. In another embodiment, the imaging sensor assembly includes at least one imaging sensor package disposed on the at least one substrate. In another embodiment, the at least one imaging sensor package includes at least one imaging sensor disposed on at least one imaging sensor package substrate. In another embodiment, the imaging sensor assembly includes at least one receiver package disposed on the at least one substrate. In another embodiment, the receiver package includes at least one receiver integrated circuit disposed on at least one receiver package substrate. In another embodiment, the imaging sensor assembly includes at least one electrical interconnect. In another embodiment, the at least one electrical interconnect is operably coupled to the at least one imaging sensor package and the at least one receiver package. In another embodiment, a plurality of data signals are transmitted between the at least one imaging sensor package and the at least one receiver package via the at least one electrical interconnect.

An imaging sensor array is disclosed, in accordance with one or more embodiments of the present disclosure. In one embodiment, the imaging sensor array includes one or more optical elements configured to at least one of reflect or scatter light. In another embodiment, the imaging sensor array includes a first imaging sensor assembly. In another embodiment, the first imaging sensor assembly includes at least one substrate. In another embodiment, the at least one substrate includes a plurality of substrate signal lines. In another embodiment, the first imaging sensor assembly includes at least one imaging sensor package disposed on the at least one substrate. In another embodiment, the at least one imaging sensor package includes at least one imaging sensor disposed on at least one imaging sensor package substrate. In another embodiment, the at least one imaging sensor package is arranged to receive at least a portion of the light from the optical element via the at least one imaging sensor. In another embodiment, the at least one imaging sensor package converts the received at least a portion of the light from the optical element into a first plurality of data signals. In another embodiment, the imaging sensor array includes at least a second imaging sensor assembly. In another embodiment, the at least a second imaging sensor assembly includes at least one substrate. In another embodiment, the at least one substrate includes a plurality of substrate signal lines. In another embodiment, the at least a second imaging sensor assembly includes at least one imaging sensor package disposed on at least one substrate. In another embodiment, the at least one imaging sensor package includes at least one imaging sensor disposed on at least one imaging sensor package substrate. In another embodiment, the at least one imaging sensor package is disposed on the at least one substrate. In another embodiment, the at least one imaging sensor package is arranged to receive at least a portion of the light from the one or more optical elements via the at least one imaging sensor. In another embodiment, the at least one imaging sensor package converts the received at least a portion of the light from the optical element into at least a second plurality of data signals. In another embodiment, the at least a second imaging sensor assembly includes at least one electrical interconnect. In another embodiment, the at least one electrical interconnect is operably coupled to the first imaging sensor assembly and the at least a second imaging sensor assembly.

A high-speed inspection system is disclosed, in accordance with one or more embodiments of the present disclosure. In one embodiment, the high-speed inspection system includes an illumination source configured to generate a first beam of illumination. In another embodiment, the high-speed inspection system includes a set of focusing optics configured to direct the first beam of illumination onto a surface of a sample. In another embodiment, the sample is secured on a sample stage. In another embodiment, the high-speed inspection system includes at least one detector configured to detect a second beam of illumination reflected or scattered from the surface of the sample in response to at least a portion of the first beam of illumination. In another embodiment, the at least one detector includes at least one imaging sensor assembly. In another embodiment, the at least one imaging sensor assembly includes at least one substrate. In another embodiment, the at least one substrate includes a plurality of substrate signal lines. In another embodiment, the at least one imaging sensor assembly includes at least one imaging sensor package disposed on the at least one substrate. In another embodiment, the at least one imaging sensor package includes at least one imaging sensor disposed on at least one imaging sensor package substrate. In another embodiment, the at least one imaging sensor assembly includes at least one receiver package disposed on the at least one substrate. In another embodiment, the receiver package includes at least one receiver integrated circuit disposed on at least one receiver package substrate. In another embodiment, the at least one imaging sensor assembly includes at least one electrical interconnect. In another embodiment, the at least one electrical interconnect is operably coupled to the at least one imaging sensor package and the at least one receiver package. In another embodiment, a plurality of data signals are transmitted between the at least one imaging sensor package and the at least one receiver package via the at least one electrical interconnect. In another embodiment, the high-speed inspection system includes a set of collection optics configured to direct the second beam of illumination reflected or scattered from the surface of the sample to the at least one detector.

It is to be understood that both the foregoing general description and the following detailed description are exemplary and explanatory only and are not necessarily restrictive of the present disclosure. The accompanying drawings, which are incorporated in and constitute a part of the characteristic, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

Referring generally to FIGS. 1-6, an assembly for high-speed image sensor data transfer is disclosed, in accordance with one or more embodiments of the present disclosure.

Embodiments of the present disclosure are directed to an image sensor assembly for high-speed data transfer. Additional embodiments of the present disclosure are also directed to an imaging sensor and signal routing assembly for the image sensor assembly. Additional embodiments of the present disclosure are directed to a high-speed imaging system including an image sensor assembly for high-speed data transfer. It is noted herein that the terms "imaging sensor" and "scanning sensor" may be considered equivalent for purposes of the present disclosure. It is additionally noted herein that an "inspection system" and a "metrology system" may be considered equivalent systems for purposes of the present disclosure.

Figure 1:
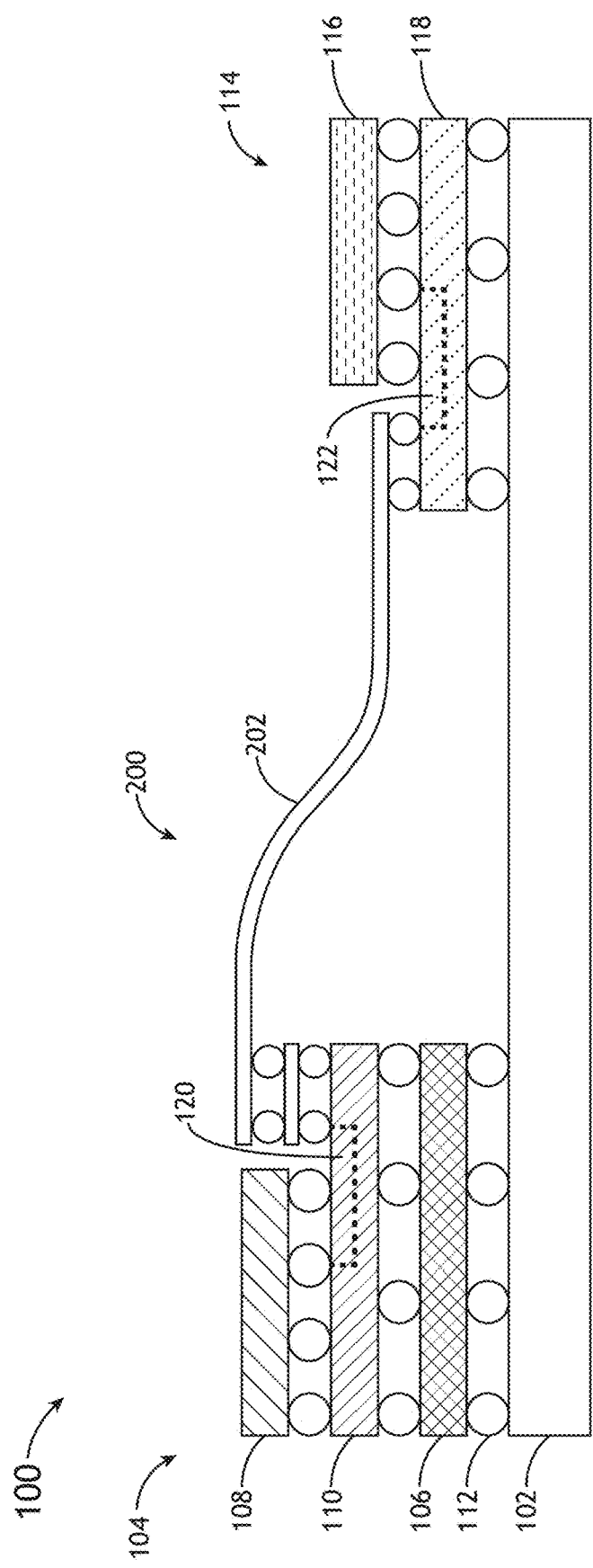
FIG. 1 illustrates a simplified schematic view of an imaging sensor assembly, in accordance with one or more embodiments of the present disclosure.

FIG. 1 illustrates a simplified schematic view of an imaging sensor assembly 100, in accordance with one or more embodiments of the present disclosure.

In one embodiment, the imaging sensor assembly 100 includes one or more substrates 102. For example, the one or more substrates 102 may include, but are not limited to, one or more printed circuit boards (PCB) 102. In another embodiment, the imaging sensor assembly 100 includes one or more integrated circuit packages. For example, the one or more integrated circuit packages may include one or more imaging sensor packages 104. By way of another example, the one or more integrated circuit packages may include one or more receiver packages 114.

In another embodiment, the one or more imaging sensor packages 104 include one or more imaging sensors 108 disposed on one or more package substrates 110. In another embodiment, the one or more imaging sensor packages 104 are disposed on one or more interposers 106, where the one or more interposers 106 are disposed on the one or more PCB 102. In another embodiment, the imaging sensor assembly 100 includes one or more receiver packages 114. In another embodiment, the one or more receiver packages 114 include one or more receiver integrated circuits 116 disposed on one or more package substrates 118.

In another embodiment, the one or more imaging sensor packages 104 and the one or more receiver packages 114 are operably coupled together via one or more signal routing assemblies 200. In another embodiment, the one or more signal routing assemblies 200 include one or more electrical interconnects 202.

The one or more PCB 102 may be any type of PCB known in the art. For example, the one or more PCB 102 may be FR4-grade PCB. By way of another example, the one or more PCB 102 may be fabricated from a ceramic. For instance, the ceramic may include, but is not limited to, a low thermal-conductivity ceramic. It is noted herein the low thermal conductivity ceramic may enable localized heating of solder-mounted components of the imaging sensor assembly 100 in sequential solder reflow steps for a high yield during fabrication.

In another embodiment, the one or more PCB 102 includes one or more substrate signal lines for transferring one or more of power, drive, low-speed control, and/or high-speed data signals between one or more components of the imaging sensor assembly 100. For example, the one or more substrate signal lines may be on a surface of the one or more PCB 102 and/or embedded within the one or more PCB 102. In another embodiment, the one or more PCB 102 include one or more area interconnect locations. For example, the one or more area interconnect locations may include, but are not limited to, one or more surface-mount packaging arrays for integrated circuits (e.g. one or more land grid arrays (LGA), one or more ball grid arrays (BGA), and/or one or more pin grid arrays (PGA).

In another embodiment, the design of the one or more PCB 102 is dependent on the electrical and/or spatial (e.g. shape and/or size) concerns of the imaging sensor assembly 100. In another embodiment, the fabrication processes utilized to produce the one or more PCB 102 are dependent on the electrical and/or spatial (e.g. shape and/or size) concerns of the imaging sensor assembly 100. For example, the fabrication processes utilized to produce the one or more PCB 102 may include, but are not limited to, one or more low-cost PCB fabrication processes (e.g. processes that do not produce specialized and/or space-constrained signal routes) and/or one or more advanced PCB fabrication processes (e.g. processes that produce specialized and/or space-constrained signal routes).

The one or more imaging sensors 108 may be any type of imaging sensor known in the art configured to capture an incident light beam (e.g. a beam of illumination). For example, the one or more imaging sensors 108 may include, but are not limited to, one or more charged coupled devices (CCDs). For instance, the one or more one or more imaging sensors 108 may be time-delay integration (TDI)-based devices. In this regard, an array of pixels may constitute an imaging region of the one or more imaging sensors 108. TDI-based imaging sensors are described generally in U.S. Pat. No. 7,609,309, issued on Oct. 27, 2009, which is incorporated herein by reference in its entirety.

The one or more interposers 106 may be any type of interposer known in the art. For example, the one or more interposers 106 may include, but are not limited to, silicon interposers. In another embodiment, the one or more interposers 106 include one or more layers. In another embodiment, one or more interposer signal lines are embedded within the one or more layers. In another embodiment, the one or more interposers 106 include one or more contact pads, where the one or more contact pads are disposed on the one or more embedded interposer signal lines with one or more signal vias. The structure and fabrication of an interposer is described in further detail in U.S. Pat. No. 8,748,828, issued on Jun. 10, 2014, which is incorporated herein in its entirety.

The one or more receiver packages 114 may include any receiver integrated circuit 116 known in the art. For example, the one or more receiver integrated circuits 116 may include, but are not limited to, one or more transceivers (e.g. one or more optical transceivers). By way of another example, the one or more receiver integrated circuits 116 may include, but are not limited to, one or more field-programmable gate arrays (FPGA), one or more memory devices, and/or one or more processors. In another embodiment, the one or more receiver packages 114 are one or more additional imaging sensor packages 104.

Although not shown, it is noted herein the one or more receiver packages 114 may be disposed on one or more interposers 106, where the one or more interposers 106 are disposed on the one or more PCB 102. Therefore, the above description should not be interpreted as a limitation on the scope of the present disclosure but merely an illustration.

In another embodiment, the package substrates 110, 118 are PCB-based devices. It is noted herein, however, that the package substrates 110, 118 may be interposers. Therefore, the above description should not be interpreted as a limitation on the scope of the present disclosure but merely an illustration.

In another embodiment, the one or more signal routing assemblies 200 transfer data at high speeds between the one or more image sensor packages 104 and the one or more receiver packages 114. For example, data may be transmitted from the one or more imaging sensors 108 to the one or more electrical interconnects 202 via one or more packaging substrate signal lines 120 embedded within the one or more package substrates 110. By way of another example, data may be transmitted from the one or more electrical interconnects 202 to the one or more receiver integrated circuits 116 via one or more packaging substrate signal lines 122 embedded within the one or more package substrates 118.

It is noted herein the high-speed data transfer made possible by the one or more electrical interconnects 202 may enable the utilizing of a larger photosensitive area of the one or more imaging sensors 108 on the one or more imaging sensor packages 104 than is possible with the possible data transfer speed via one or more area interconnects (e.g., an LGA, a BGA, and/or a PGA).

In another embodiment, one or more support structures may operably couple (e.g. electrically, mechanically, electromechanically, and/or communicatively couple) together one or more bonding surfaces (e.g. contact pads, or the like) of adjacent components of the imaging sensor assembly 100. For example, the one or more support structures may provide structural support and/or electrical interconnection to the one or more imaging sensors 108.

For example, the one or more support structures may include, but are not limited to, solder balls that couple together the one or more bonding surfaces of adjacent components of the imaging sensor assembly 100. By way of another example, the one or more support structures 112 may include, but are not limited to, a conductive film 210 that couples together the one or more bonding surfaces of adjacent components of the imaging sensor assembly 100. By way of another example, the one or more support structures 112 may include, but are not limited to, an underfill material that couples together the one or more bonding surfaces of adjacent components of the imaging sensor assembly 100. For instance, an epoxy resin may be disposed between the bonding surfaces of adjacent imaging sensor assembly 100 components.

It is noted herein that the integrated circuit packages on the imaging sensor assembly 100 may be small and/or not designed for large amounts of mechanical stress. As such, the one or more imaging sensor assemblies 100 may include, but are not limited to, one or more braised connections and/or specially-machined integrated circuit packages. It is additionally noted herein the one or more imaging sensor assemblies 100 may include, but are not limited to, one or more drilled-through holes and/or one or more threaded inserts that couple together the one or more bonding surfaces of adjacent components of the imaging sensor assembly 100. It is noted herein that a threaded insert with a bolt-on connection may be suitable for application where re-fabrication of the imaging sensor assemblies 100 is necessary due to increased rates of possible damage during fabrication, and/or generally to improve yield during the fabrication process.

Figure 2A:
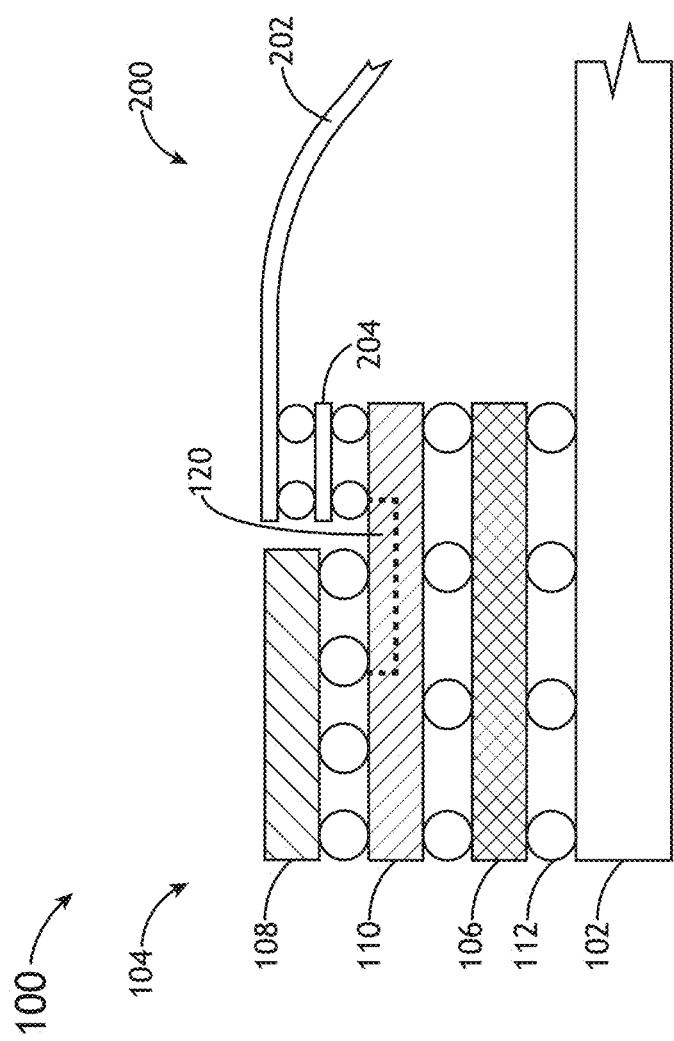
FIG. 2A illustrates a simplified schematic view of an imaging sensor package and signal routing assembly of an imaging sensor assembly, in accordance with one or more embodiments of the present disclosure.
Figure 2B:
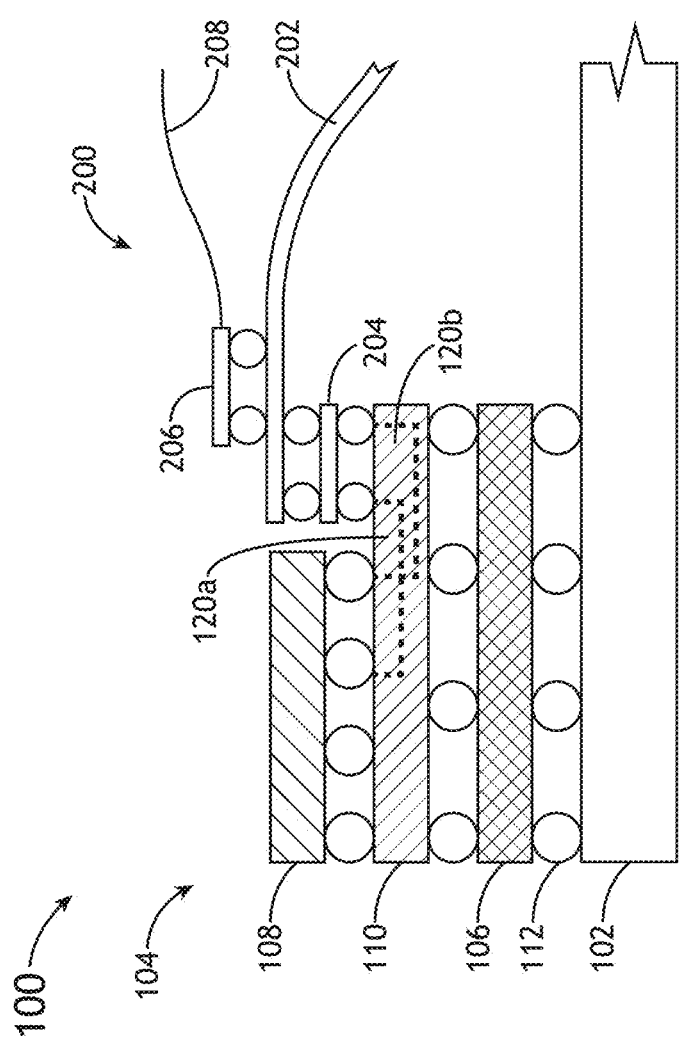
FIG. 2B illustrates a simplified schematic view of an imaging sensor package and signal routing assembly of an imaging sensor assembly, in accordance with one or more embodiments of the present disclosure.
Figure 2C:
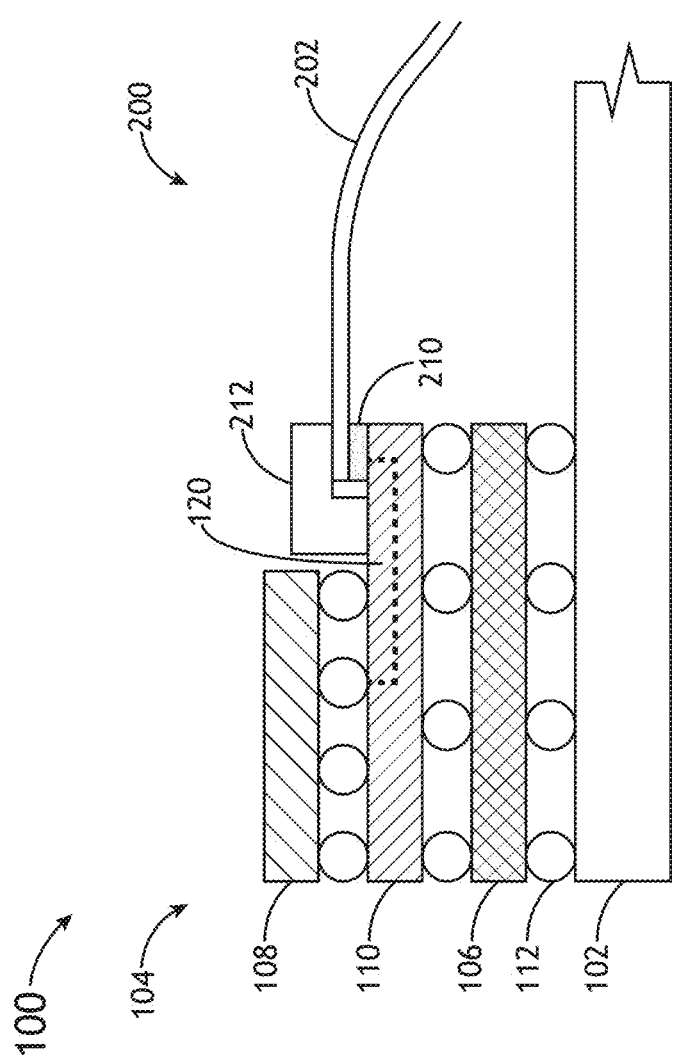
FIG. 2C illustrates a simplified schematic view of an imaging sensor package and signal routing assembly of an imaging sensor assembly, in accordance with one or more embodiments of the present disclosure.

FIGS. 2A-2C illustrate simplified schematic views of the imaging sensor package 104 and the signal routing assembly 200 of the imaging sensor assembly 100, in accordance with one or more embodiments of the present disclosure.

In one embodiment, the one or more electrical interconnects 202 are PCB structures. For example, the one or more electrical interconnects 202 may include, but are not limited to, flexible circuit (e.g., Flex Circuit) and/or rigid PCB. In another embodiment, the one or more electrical interconnects 202 are cable structures. For example, the one or more electrical interconnects 202 may include, but are not limited to, ribbon cable, wires, clustered electrical connector cables, and/or non-clustered (e.g., standalone) electrical connector cables.

In another embodiment, one or more high-speed data lines are routed through the one or more electrical interconnects 202, while one or more power, drive, and/or low-speed control lines are routed through the one or more PCB 102 (e.g. via the interposer 106).

In another embodiment, the signal routing assembly 200 includes one or more electrical signaling components coupling the one or more electrical interconnects 202 to the one or more package substrates 110. As illustrated in FIGS. 2A and 2B, the one or more electrical interconnects 202 are attached to the one or more package substrates 110 via one or more electrical interconnect substrates 204. For example, the package substrates 110, 118 may be PCB-based devices. By way of another example, the one or more electrical interconnect substrates 204 may be interposers.

It is noted herein the one or more electrical interconnects 202 may be attached directly to the one or more package substrates 110, such that the one or more electrical interconnect substrates 204 are not necessary. Therefore, the above description should not be interpreted as a limitation on the scope of the present disclosure but merely an illustration.

Figure 6:
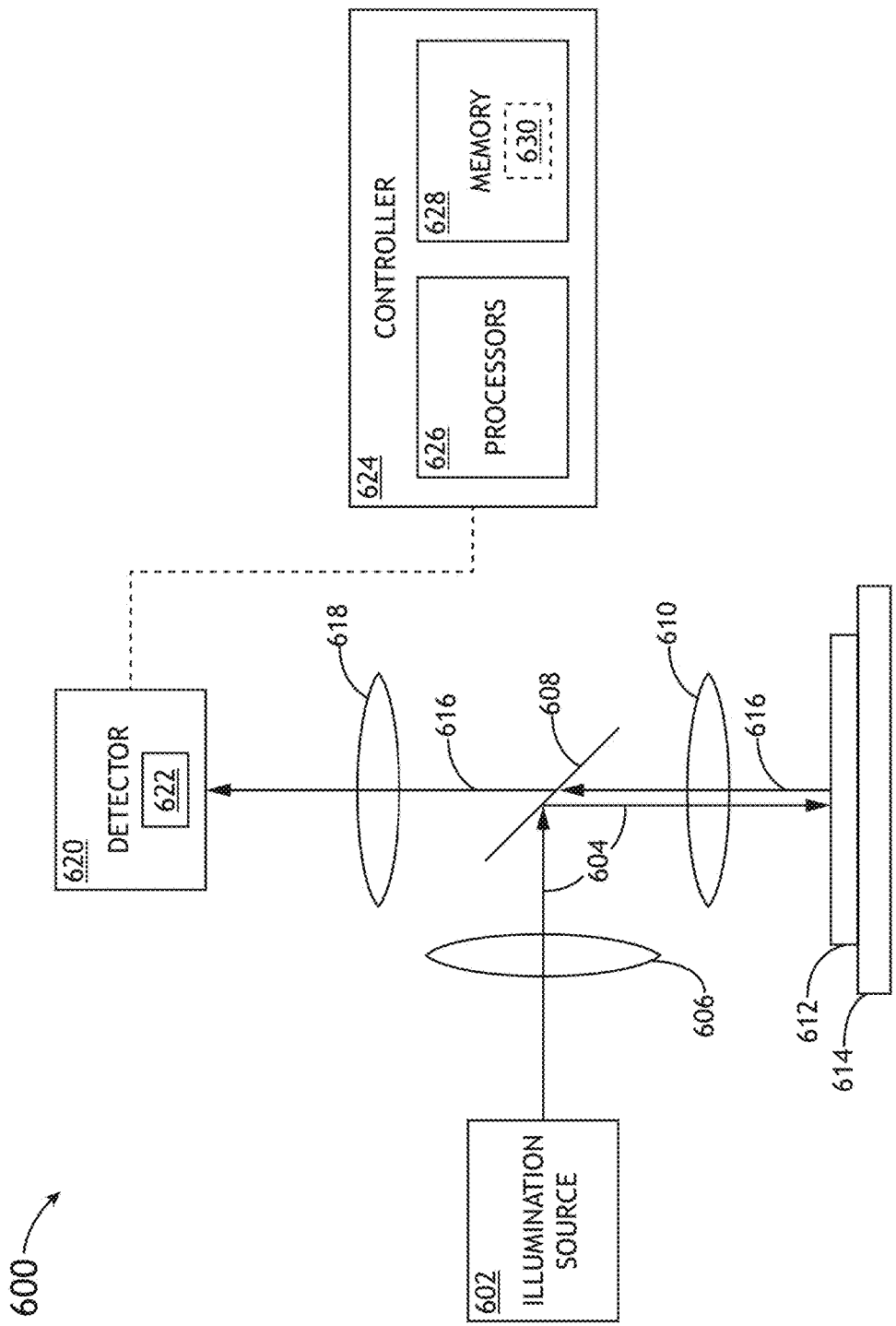
FIG. 6 illustrates a simplified schematic view of an imaging system, in accordance with one or more embodiments of the present disclosure.

In another embodiment, the signal routing assembly 200 includes one or more optical signaling components. As illustrated in FIG. 2B, one or more optical fibers 208 are attached to the one or more electrical interconnects 202 via one or more transceivers 206 (e.g. optical transceivers) mounted to the one or more electrical interconnects 202. For example, the one or more transceivers 206 may allow for high-speed communication of imaging data between the one or more imaging sensors 108 and accompanying inspection components of an inspection system 600, as illustrated in FIG. 6.

In another embodiment, mounting the one or more transceivers 206 to the one or more electrical interconnects 202 allows for one or more power, drive, and/or low-speed control lines to be routed through the one or more electrical interconnects 202 to the one or more transceivers 206 instead of through the one or more package substrates 110. In this regard, only the high-speed data lines are routed through the one or more package substrates 110. For example, data may be transmitted from the one or more imaging sensors 108 to the one or more signal routing assemblies through the one or more electrical interconnects 202 via one or more packaging substrate signal lines 120a, 120b embedded within the one or more package substrates 110.

It is noted herein that routing the one or more power, drive and/or low-speed control lines through the one or more electrical interconnects 202 allows for the required number of connections between the one or more package substrates 110 and the one or more transceivers 206 to be reduced. Additionally, the numbers of layers of the one or more package substrates 110, as well as the complexity of the routing design through those layers, may be reduced.

By way of another example, the one or more transceivers 206 may be directly mounted to the one or more package substrates 110 instead of to the one or more electrical interconnects 202. In this example, one or more power, drive, low-speed control lines, and/or high-speed data lines may be routed through the one or more package substrates 110. It is noted herein, however, that this arrangement is slower and more design-restrictive than mounting the one or more transceivers 206 to the one or more electrical interconnects 202.

In another embodiment, the optical signaling components included in the signal routing assembly 200 require an optical driver-and-receiver pair at each end of the signal routing assembly 200, to convert electrical signals to optical signals and to convert optical signals back into electrical signals.

In another embodiment, the signal routing assembly 200 is operably coupled to the one or more imaging sensor packages 104 via the one or more support structures 112. As illustrated in FIG. 2C, the one or more electrical interconnects 202 are attached to the one or more package substrates 110 via the conductive film 210 and a clamp assembly 212. For example, the conductive film 210 may include, but is not limited to, an anisotropic conductive film. In another embodiment, the conductive film 210 provides a high-performance, densely-packed electrical interconnection between the one or more electrical interconnects 202 and the one or more package substrates 110.

In another embodiment, although not shown, the signal routing assembly 200 includes the one or more transceivers 206 and the one or more electrical interconnects 202 are operably coupled to the one or more package substrates 110 via the conductive film 210.

In another embodiment, the one or more electrical interconnects 202 reduce the need for routing signals through the one or more PCB 102. For example, the one or more electrical interconnects 202 may facilitate the routing of high-speed signals between the one or more imaging sensor packages 104 of the imaging assembly 100. By way of another example, the one or more electrical interconnects 202 may allow for a high-density clustering of electrical interconnects not possible when routing signal through the one or more PCB 102.

It is noted herein that all discussion related to coupling the one or more electrical interconnects 202 to the one or more package substrates 110 may be extended to coupling the one or more electrical interconnects 202 to the one or more package substrates 118. Therefore, the above description should not be interpreted as a limitation on the scope of the present disclosure but merely an illustration.

Figure 3:
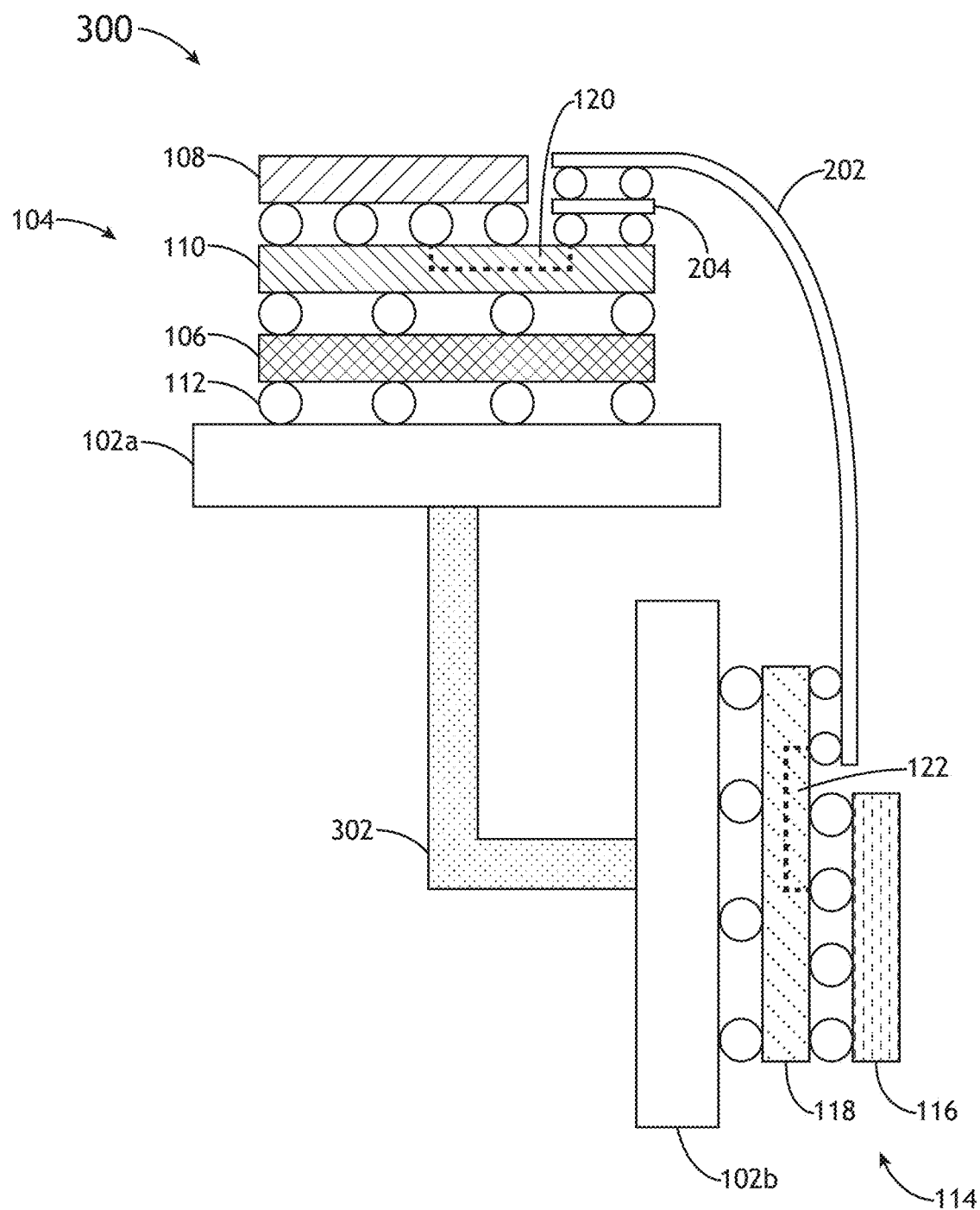
FIG. 3 illustrates a simplified schematic view of an imaging sensor assembly, in accordance with one or more embodiments of the present disclosure.

FIG. 3 illustrates a simplified schematic view of an imaging sensor assembly 300, in accordance with one or more embodiments of the present disclosure.

In one embodiment, the one or more PCB 102 includes a first PCB 102a and a second PCB 102b. For example, the one or more imaging sensor packages 104 may be disposed on the first PCB 102a (e.g. via one or more interposers 106). By way of another example, the one or more receiver packages 114 may be disposed on the second PCB 102b.

In another embodiment, the signal routing assembly 200 couples the one or more imaging sensor packages 104 on the first PCB 102a (e.g. via the interposer 106) to the one or more receiver packages 114 on the second PCB 102b. In another embodiment, one or more electrical interconnects 302 may couple the first PCB 102a to the second PCB 102b. For example, the one or more electrical interconnects 302 may include, but are not limited to, ribbon cable, wires, clustered electrical connector cables, and/or non-clustered (e.g. standalone) electrical connector cables.

In another embodiment, the high-speed and low-speed signals are separated between the signal routing assembly 200 and the one or more electrical interconnects 302. For example, in another embodiment, high-speed data lines may be routed through the one or more electrical interconnects 202, while one or more power, drive, and/or low-speed control lines may be routed through the one or more electrical interconnects 302. In this regard, PCB design complexity and PCB-connector density is reduced. Additionally, the required bandwidth for the signals is reduced.

In another embodiment, where the one or more electrical interconnects 202 include Flex Circuit, the PCB 102a, 102b are oriented relative to one another at an angle. For example, the PCB 102a, 102b may be oriented relative to one another at a custom angle including, but not limited to, a custom angle ranging from 1-179 degrees. By way of another example, as illustrated in FIG. 3, the angle may be substantially oriented at a 90 degree angle.

It another embodiment, where the one or more electrical interconnects 202 include Flex Circuit, the PCB 102a including the one or more imaging sensor packages 104 may be displaced and/or rotated with respect to the PCB 102b including the one or more receiver packages 114 (and the rest of the optical system).

It is noted herein that multiple PCB 102 may be implemented in size and/or space-constrained imaging devices requiring complex, multi-PCB configurations.

Figure 4:
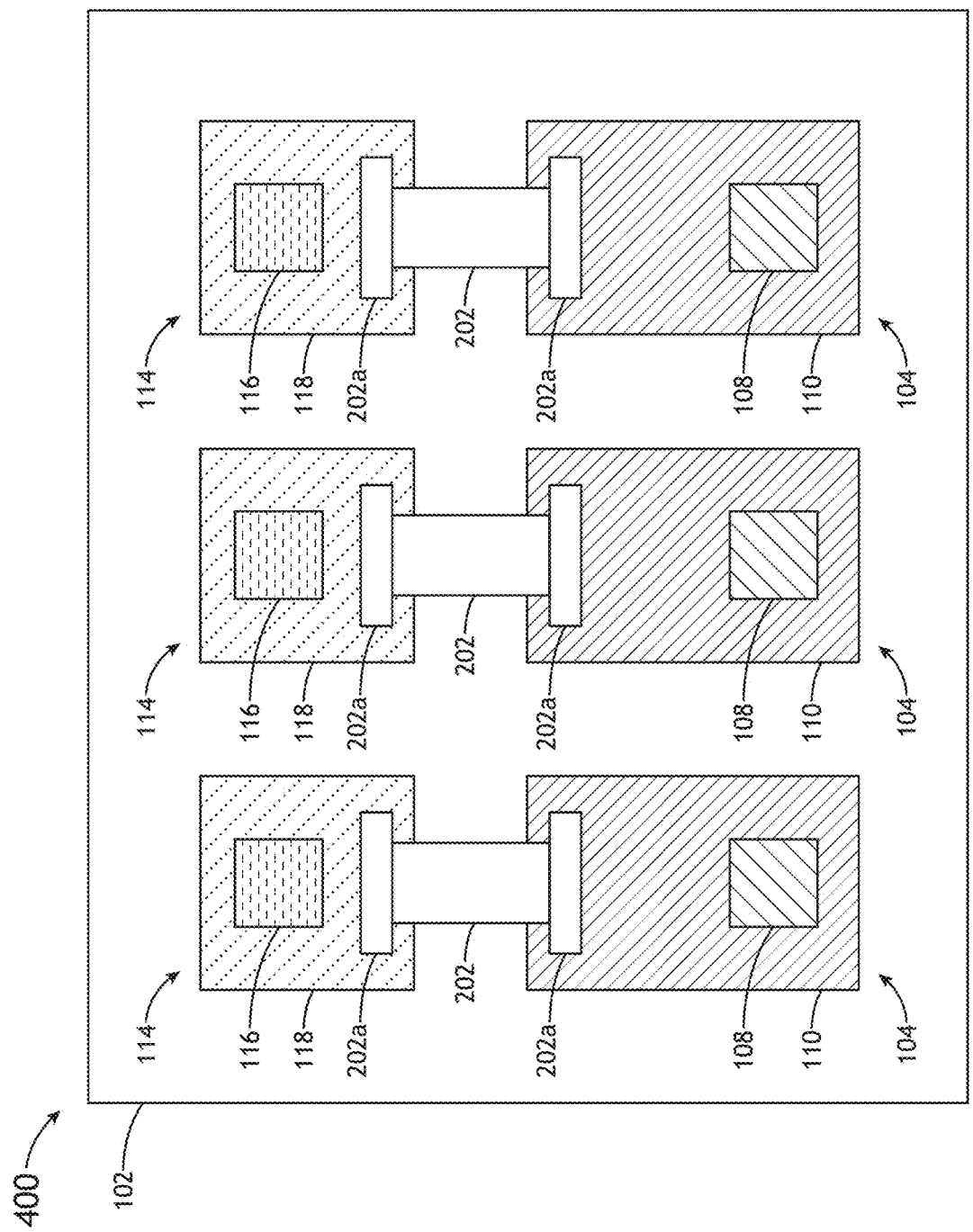
FIG. 4 illustrates a simplified schematic view of an array including a set of imaging sensor assemblies, in accordance with one or more embodiments of the present disclosure.

FIG. 4 illustrates a simplified schematic view of an array 400 including a set of imaging sensor assemblies 100, in accordance with one or more embodiments of the present disclosure.

In one embodiment, the array 400 includes a set of imaging sensor assemblies 100 disposed on the one or more PCB 102. In another embodiment, the set of imaging sensor assemblies 100 includes one or more imaging sensor packages 104 operably coupled to one or more receiver packages 114 via one or more signal routing assemblies 200, where the one or more signal routing assemblies 200 include one or more electrical interconnects 202. In another embodiment, the one or more electrical interconnects 202 are operably coupled to the one or more imaging sensor packages 104 and the one or more receiver packages 114 via one or more support structures 202a.

It is noted herein the one or more support structures 112 should be interpreted to apply to the one or more support structures 202a for purposes of the present disclosure. It is additionally noted herein the one or more electrical signaling components coupling the one or more electrical interconnects 202 to the one or more package substrates 110, as illustrated in FIGS. 2A-2C, should be interpreted to apply to the one or more support structures 202a for purposes of the present disclosure.

In another embodiment, the one or more receiver packages 114 include one or more receiver integrated circuits 116. For example, the one or more receiver integrated circuits 116 may include, but are not limited to, one or more transceivers (e.g., one or more optical transceivers), one or more FPGA devices, one or more memory devices, and/or one or more processors disposed on one or more receiver package substrates 118. In this regard, cost is reduced while increasing fabrication yield, as the PCB 102 may include a more modular (e.g., less complex) design centered on replaceable integrated circuit packages.

In another embodiment, one or more low-speed substrate signal lines are located on a surface of, or embedded within, the PCB 102. In another embodiment, the one or more low-speed substrate signal lines are operably coupled to the one or more integrated circuit packages of the one or more imaging sensor assemblies 100. For example, the one or more low-speed substrate signal lines may provide one or more power, drive, and/or low-speed control signals to the one or more imaging sensor packages 104. By way of another example, the one or more low-speed substrate signal lines may provide one or more power, drive, and/or low-speed control signals to the one or more receiver packages 114. For instance, the power, drive, and/or low-speed control signals provided to the one or more receiver packages 114 may be the same or different from the one or more power, drive, and/or low-speed control signals provided to the one or more imaging sensor packages 104.

In this regard, the high-speed and low-speed signals for the one or more imaging sensor assemblies 100 may be separated between the signal routing assembly 200 and the one or more low-speed substrate signal lines. It is noted herein that while high-speed electrical interconnects may additionally be located on the surface of, or embedded within, the PCB 102, those high-speed electrical interconnects will typically require advanced PCB designs and special fabrication materials.

Figure 5:
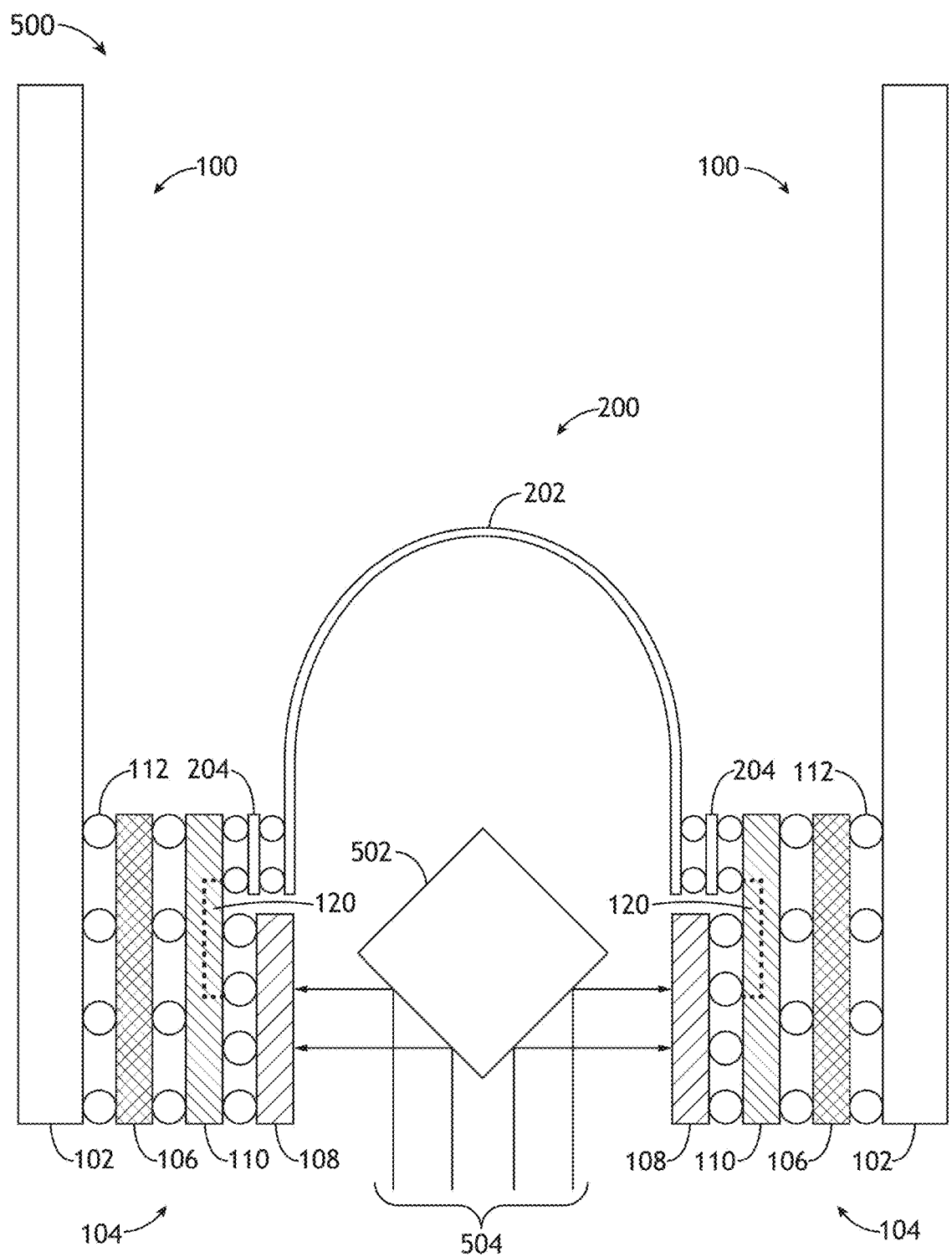
FIG. 5 illustrates a simplified schematic view of a modular array including a set of imaging sensor assemblies, in accordance with one or more embodiments of the present disclosure.

FIG. 5 illustrates a simplified schematic view of a modular array 500 including a set of imaging sensor assemblies 100, in accordance with one or more embodiments of the present disclosure.

In one embodiment, the set of imaging sensor assemblies 100 of the modular array 500 includes a first imaging sensor assembly 100 and at least a second imaging sensor assembly 100. In another embodiment, the one or more imaging sensor packages 104 of the first imaging sensor assembly 100 are coupled to the one or more imaging sensor packages 104 of the at least a second imaging sensor assembly 100 via the one or more electrical interconnects 202 of the signal routing assembly 200.

In another embodiment, the set of imaging sensor assemblies 100 surrounds one or more optical elements 502. For example, the one or more optical elements 502 may include, but are not limited to, one or more prisms, one or more beam deflectors, and/or one or more beam splitters. In another embodiment, the set of imaging sensor assemblies 100 are oriented to receive light 504 reflected from the one or more optical elements 502 via the one or more imaging sensors 108. For example, the one or more imaging sensor assemblies 100 may be positioned in a tiled formation around the one or more optical elements 502. In another embodiment, the set of imaging sensor assemblies 100 converts the received light 504 from the one or more optical elements 502 into one or more sets of data signals.

In another embodiment, the one or more electrical interconnects 202 of the signal routing assembly 200 combines the one or more sets of data signals from the set of imaging sensor assemblies 100 in the modular array 500 into an aggregated data stream. In this regard, the one or more electrical interconnects 202 may provide flexibility with respect to the positioning precision of the one or more imaging sensor assemblies 100 within the modular array 500. Additionally, coupling the one or more imaging sensor assemblies 100 together via one or more electrical interconnects 202 may allow for real-time data transfer between the one or more imaging sensor assemblies 100, despite the one or more imaging sensor assemblies 100 being positioned a selected distance apart. Further, coupling the one or more imaging sensor assemblies 100 via one or more electrical interconnects 202 may allow for point-to-point communication directly between the one or more imaging sensor assemblies 100 without adding complexity to the design of the one or more PCB 102 of the one or more imaging sensor assemblies 100.

In another embodiment, one or more of the first imaging sensor assembly 100 and the at least a second imaging sensor assembly 100 may include multiple imaging sensor packages 104. For example, one or more imaging sensor packages 104 may be disposed on one or more imaging sensor packages 104 on the same PCB 102, and one or more imaging sensor packages 104 additionally may be disposed on a separate PCB 102.

In another embodiment, one or more of the first imaging sensor assembly 100 and the at least a second imaging sensor assembly 100 may include one or more receiver packages 114. For example, one or more imaging sensor packages 104 may be coupled to one or more receiver packages 114 on the same PCB 102, and additionally may be coupled to one or more imaging sensor packages 104 on separate PCB 102.

It is noted herein that any portion of the design and/or components of the assembly 300 and the arrays 400 and 500 may be combined to form an imaging sensor assembly. Therefore, the above description should not be interpreted as a limitation on the scope of the present disclosure but merely an illustration.

FIG. 6 illustrates a simplified schematic view of an inspection system 600, in accordance with one or more embodiments of the present disclosure.

The inspection system 600 may include any metrology system or inspection system known in the art. For example, the inspection system 600 may include any appropriate characterization tool known in the art such as, but not limited to, an inspection system or review tool. For example, the inspection system 600 may include, but is not limited to, an electron beam inspection or review tool (e.g., a Scanning Electron Microscope (SEM) system). By way of another example, the inspection system 600 may include, but is not limited to, an optical inspection sub-system. For instance, the optical inspection sub-system may include an optical inspection sub-system capable of generating one or more high-resolution images representing the electrical intent of the sample 612. Additionally, the optical inspection sub-system may include a broadband inspection sub-system including, but not limited to, a laser sustained plasma (LSP) based inspection sub-system. Further, the optical inspection sub-system may include a narrowband inspection sub-system, such as, but not limited to, a laser scanning inspection sub-system. Further, the optical inspection sub-system may include, but is not limited to, a brightfield imaging tool, or a darkfield imaging tool. It is noted herein that the inspection system 600 may include any optical system configured to collect and analyze illumination reflected, scattered, diffracted, and/or radiated from a surface of a sample 612. In a general sense, although not shown here, the inspection system 600 may include any inspection system suitable for inspecting one or more wafers, reticles, or photomasks.

In one embodiment, the inspection system 600 includes an illumination source 602. The illumination source 602 may include any illumination source known in the art. For example, the illumination source 602 may include, but is not limited to, a broadband light source (e.g. a Xenon lamp) or a narrowband light source (e.g. a laser). By way of another example, the illumination source 602 may be configured to generate EUV light. For instance, the EUV light source may include a discharge produced plasma (DPP) light source or a laser produced plasma (LPP) light source configured to generate light in the EUV range.

In another embodiment, the illumination source 602 generates and directs light 604 (e.g. a beam of illumination) to the surface of the sample 612 disposed on the sample stage 614. For example, the illumination source 602 may be configured to direct light to the surface of the sample 612 disposed on the sample stage 614 via one or more of a set of optical elements 606, a beam splitter 608, and/or a set of optical elements 610. It is noted herein the set of optical elements 606 and/or the set of optical elements 610 may include any optical element known in the art suitable for focusing, suppressing, extracting, and/or directing the light 604. It is additionally noted herein the set of optical elements 606, the beam splitter 608, and the set of optical elements 610 may be considered to be a set of focusing optics for purposes of the present disclosure.

The sample 612 may include any sample suitable for optical inspection and/or review. In one embodiment, the sample includes a wafer. For example, the sample may include, but is not limited to, a semiconductor wafer. As used through the present disclosure, the term "wafer" refers to a substrate formed of a semiconductor and/or a non-semiconductor material. For instance, in the case of a semiconductor material, the wafer may be formed from, but is not limited to, monocrystalline silicon, gallium arsenide, and/or indium phosphide. In another embodiment, the sample includes a photomask/reticle.

In another embodiment, the sample 612 is manufactured using one or more sets of wafer design data. In another embodiment, the sets of wafer design data include one or more sets of layers. For example, such layers may include, but are not limited to, a resist, a dielectric material, a conductive material, and a semi-conductive material. Many different types of such layers are known in the art, and the term wafer as used herein is intended to encompass a wafer on which all types of such layers may be formed. By way of another example, the layers formed on the wafer may be repeated one or more times within the wafer. Formation and processing of such layers of material may ultimately result in completed devices. Many different types of devices may be formed on a wafer, and the term wafer as used herein is intended to encompass a wafer on which any type of device known in the art is being fabricated.

The sample stage 614 may include any appropriate mechanical and/or robotic assembly known in the art of electron-beam microscopy. In one embodiment, the sample stage 614 is an actuatable stage. For example, the sample stage 614 may include, but is not limited to, one or more translational stages suitable for selectably translating the sample 612 along one or more linear directions (e.g., x-direction, y-direction, and/or z-direction). By way of another example, the sample stage 614 may include, but is not limited to, one or more rotational stages suitable for selectively rotating the sample 612 along a rotational direction. By way of another example, the sample stage 614 may include, but is not limited to, a rotational stage and a translational stage suitable for selectably translating the sample along a linear direction and/or rotating the sample 612 along a rotational direction. By way of another example, the sample stage 614 may be configured to translate or rotate the sample 612 for positioning, focusing, and/or scanning in accordance with a selected inspection or metrology algorithm, several of which are known to the art.

In another embodiment, the inspection system 600 is configured to detect one or more defects in the sample 612. For purposes of the present disclosure, a defect may be classified as a void, short, particle, residue, scum, or any other defect known in the art.

In another embodiment, the inspection system 600 detects defects on the sample 612 via one or more detectors 620. The one or more detectors 620 may be any detector known in the art. For example, the one or more detectors 620 may include, but is not limited to, photo-multiplier tubes (PMTs), charge coupled devices (CCDs), a time-delay integration (TDI) camera, and the like. In addition, the output of the one or more detectors 620 may be operably coupled to a controller 624, as described in detail further herein.

In another embodiment, the sample 612 reflects, scatters, diffracts, and/or radiates light 616 (e.g. a beam of illumination) in response to the light 604. In another embodiment, the light 616 is directed to the one or more detectors 620. For example, the light 616 may be directed to one or more detectors 620 via one or more of the set of optical elements 610, the beam splitter 608, and/or a set of optical elements 618. It is noted herein the set of optical elements 610 and/or the set of optical elements 618 may include any optical element known in the art suitable for focusing, suppressing, extracting, and/or directing the light 616. It is additionally noted herein the set of optical elements 610, the beam splitter 608 and the set of optical elements 618 may be considered to be a set of collection optics for purposes of the present disclosure.

In another embodiment, the one or more detectors 620 include one or more imaging sensor assemblies 622. For example, the one or more detectors 620 may include the imaging sensor assemblies 100 and 300 (and the corresponding optical hardware as required by the assemblies 100 and 300), as illustrated in FIGS. 1 and 3, respectively. By way of another example, the detector 620 may include the arrays 400 and 500 including one or more imaging sensor assemblies 100 (and the corresponding optical hardware as required by the array 400 and 500), as illustrated in FIGS. 4 and 5, respectively. In this regard, the description of the imaging sensor assemblies 100 and 300, and the arrays 400 and 500, should be interpreted to apply to the one or more imaging sensor assemblies 622 of the inspection system 600.

In one embodiment, the inspection system 600 includes the controller 624. In another embodiment, the controller 624 is operably coupled to one or more components of the inspection system 600. For example, the controller 624 may be operably coupled to the illumination source 602, the sample stage 614, and/or the one or more detectors 620. In this regard, the controller 624 may direct any of the components of the inspection system 600 to carry out any one or more of the various functions described throughout the present disclosure. In another embodiment, the controller 624 includes one or more processors 626 and memory 628. The memory 628 may store one or more sets of program instructions 630.

The controller 624 may be configured to receive and/or acquire data or information from other systems or subsystems (e.g., one or more sets of information from the illumination source 602, the sample stage 614, and/or the one or more detectors 620) of the inspection system 600 by a transmission medium that may include wireline and/or wireless portions. The controller 624 may additionally be configured to transmit data or information (e.g., the output of one or more procedures of the inventive concepts disclosed herein) to one or more systems or sub-systems (e.g., one or more sets of information from the illumination source 602, the sample stage 614, and/or the one or more detectors 620) of the inspection system 600 by a transmission medium that may include wireline and/or wireless portions. In this regard, the transmission medium may serve as a data link between the controller and the other subsystems of the inspection system 600. Additionally, the controller 624 may be configured to send data to external systems via a transmission medium (e.g., network connection).

The one or more processors 626 may include any one or more processing elements known in the art. In this sense, the one or more processors 626 may include any microprocessor device configured to execute algorithms and/or program instructions. For example, the one or more processors 626 may consist of a desktop computer, mainframe computer system, workstation, image computer, parallel processor, handheld computer (e.g. tablet, smartphone, or phablet), or other computer system (e.g., networked computer). In general, the term "processor" may be broadly defined to encompass any device having one or more processing elements, which execute the one or sets of program instructions 630 from a non-transitory memory medium (e.g., the memory 628). Moreover, different subsystems of the inspection system 600 (e.g., one or more sets of information from the illumination source 602, the sample stage 614, and/or the one or more detectors 620) may include processor or logic elements suitable for carrying out at least a portion of the steps described throughout the present disclosure. Therefore, the above description should not be interpreted as a limitation on the present disclosure but merely an illustration.

The memory 628 may include any storage medium known in the art suitable for storing the one or more sets of program instructions 630 executable by the associated one or more processors 626. For example, the memory 628 may include a non-transitory memory medium. For instance, the memory 628 may include, but is not limited to, a read-only memory, a random access memory, a magnetic or optical memory device (e.g., disk), a magnetic tape, a solid state drive, and the like. The memory 628 may be configured to provide display information to a display device of a user interface. The memory 628 may additionally be configured to store user input information from a user input device of the user interface. The memory 628 may be housed in a common controller 624 housing with the one or more processors 626.

The memory 628 may, alternatively or in addition, be located remotely with respect to the spatial location of the processors 626 and/or the controller 624. For instance, the one or more processors 626 and/or the controller 624 may access a remote memory 628 (e.g., server), accessible through a network (e.g., internet, intranet, and the like).

In one embodiment, the illumination source 602 may be operably coupled to a set of positioners configured to actuate the illumination source 602 in one or more directions. For example, the controller 624 may direct the set of positioners to translate the illumination source 602 in one or more of an x-direction, a y-direction, and/or a z-direction to correct beam misalignment produced by any of the components of the inspection system 600.

Advantages of the present disclosure include the interconnection of multiple imaging sensors via Flex Circuit to ceramic-based integrated circuit packages, where power, drive, and/or low-speed control signals are routed through the ceramic-based integrated circuit packages and high-speed data transfer signals are substantially simultaneously routed through the Flex Circuit.

Advantages of the present disclosure additionally include the use of an anisotropic conductive material for connecting the Flex Circuit to the ceramic-based integrated circuit packages.

Advantages of the present disclosure additionally include the use of Flex Circuit with optical transceiver modules, where one or more power, drive, and/or control signals for the optical transceiver modules are routed through the Flex Circuit and imaging sensor signals are substantially simultaneously routed through the ceramic-based integrated circuit packages.

Advantages of the present disclosure additionally include combining Flex Circuit and optical transceivers into a single ceramic-based integrated circuit package, where the Flex Circuit is utilized for electrical signals.

Advantages of the present disclosure additionally include utilizing Flex Circuit for output data signals and conventional PCB for one or more power, drive, and/or control signals for TDI imaging sensors.

Advantages of the present disclosure additionally include a tiled imaging system assembly utilizing Flex Circuit connections to aggregate modular imaging sensor array data into one data stream, while substantially simultaneously utilizing conventional PCB for backplane and modular imaging sensor array mounting.

Additional advantages of the present disclosure include enabling a larger photosensitive area of the imaging sensor assembly by replacing an area interconnect such as a surface-mount packaging for integrated circuits (e.g. an LGA, a BGA, and/or a PGA) with a high-density, peripheral interconnect (e.g. Flex Circuit).

Additional advantages of the present disclosure include a possibility of lateral and/or angular displacement of one or more imaging sensor assemblies 100 with respect to one another and with respect to an optical assembly to enable sensor alignment to the optical system.

Additional advantages of the present disclosure include obtaining a high product yield by utilizing a low thermal conductivity ceramic to localize heating of solder-mounted components in sequential solder-reflow steps during fabrication of the imaging sensor assemblies.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Accordingly, the scope of the invention should be limited only by the claims appended hereto.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed:

1. An imaging sensor assembly, comprising:
    at least one substrate, wherein the at least one substrate includes a plurality of substrate signal lines;
    at least one imaging sensor package disposed on the at least one substrate, wherein the at least one imaging sensor package includes at least one imaging sensor disposed on at least one imaging sensor package substrate;
    at least one receiver package disposed on the at least one substrate, wherein the receiver package includes at least one receiver integrated circuit disposed on at least one receiver package substrate, wherein the at least one receiver package and the at least one imaging sensor package are disposed a selected distance apart on the at least one substrate; and
    at least one circuit board, wherein the at least one circuit board is operably coupled at a selected distance above a surface of the at least one substrate to the at least one imaging sensor package and the at least one receiver package, wherein a plurality of data signals is transmitted between the at least one imaging sensor package and the at least one receiver package via the at least one circuit board.

2. The assembly in claim 1, wherein the at least one imaging sensor package is disposed on at least one interposer, wherein the at least one interposer is disposed on the at least one substrate.

3. The assembly in claim 1, wherein the at least one imaging sensor includes one or more of at least one charge-coupled imaging sensor or at least one time-delay integration-based imaging sensor.

4. The assembly in claim 1, wherein the at least one receiver integrated circuit includes one or more of at least one optical transceiver, at least one field-programmable gate array, at least one memory device, or at least one processor.

5. The assembly in claim 1, wherein the at least one receiver integrated circuit includes at least one imaging sensor, wherein the at least one imaging sensor includes one or more of at least one charge-coupled imaging sensor or at least one time-delay integration-based imaging sensor.

6. The assembly in claim 1, wherein the at least one circuit board comprises at least one of a flexible circuit board or a rigid circuit board.

7. The assembly in claim 1, wherein the at least one circuit board operably couples the at least one imaging sensor package substrate to the at least one receiver package substrate.

8. The assembly in claim 7, wherein the plurality of data signals is routed to the at least one circuit board from the at least one imaging sensor via a plurality of packaging substrate signal lines in the imaging sensor packaging substrate.

9. The assembly in claim 7, wherein the plurality of data signals is routed to the at least one receiver integrated circuit from the at least one circuit board via a plurality of packaging substrate signal lines in the receiver packaging substrate.

10. The assembly in claim 1, wherein the at least one circuit board is disposed on at least one electrical interconnect substrate, wherein the at least one electrical interconnect substrate is operably coupled to the at least one imaging sensor package substrate.

11. The assembly in claim 1, wherein the at least one circuit board is operably coupled to the at least one imaging sensor package substrate via at least one conductive film and clamp assembly.

12. The assembly in claim 1, wherein at least one data transceiver is disposed on the at least one circuit board, wherein the at least one circuit board is disposed on at least one electrical interconnect substrate, wherein the at least one electrical interconnect substrate is operably coupled to the at least one imaging sensor package substrate.

13. The assembly in claim 12, wherein the at least one data transceiver includes at least one optical transceiver.

14. The assembly in claim 12, wherein one or more of a plurality of power signals, a plurality of drive signals, or a plurality of control signals are transmitted to the at least one data transceiver via the at least one circuit board.

15. The assembly in claim 1, wherein the plurality of substrate signal lines of the at least one substrate includes one or more of at least one of a plurality of embedded substrate signal lines in the at least one substrate or a plurality of surface signal lines on the at least one substrate.

16. The assembly in claim 1, wherein one or more of a plurality of power signals, a plurality of drive signals, or a plurality of control signals are transmitted to one or more of the at least one imaging sensor package or the receiver package via the plurality of substrate signal lines of the at least one substrate.

17. The assembly in claim 1, wherein the at least one substrate includes a first substrate and at least a second substrate, wherein the first substrate and the at least a second substrate are operably coupled via at least one circuit board.

18. The assembly in claim 17, wherein the at least one imaging sensor package is disposed on the first substrate.

19. The assembly in claim 17, wherein the at least one receiver package is disposed on the at least a second substrate.

20. The assembly in claim 1, wherein one or more of the at least one substrate, the at least one imaging sensor integrated circuit packaging substrate, or the at least one receiver integrated circuit packaging substrate are fabricated from a low thermal conductivity ceramic.

21. An imaging sensor array, comprising:
one or more optical elements configured to at least one of reflect or scatter light;
a first imaging sensor assembly, comprising:
at least one substrate, wherein the at least one substrate includes a plurality of substrate signal lines; and
at least one imaging sensor package disposed on the at least one substrate, wherein the at least one imaging sensor package includes at least one imaging sensor disposed on at least one imaging sensor package substrate,
wherein the at least one imaging sensor package is arranged to receive at least a portion of the light from the optical element via the at least one imaging sensor,
wherein the at least one imaging sensor package converts the received at least a portion of the light from the optical element into a first plurality of data signals;
at least a second imaging sensor assembly, comprising:
at least one substrate, wherein the at least one substrate includes a plurality of substrate signal lines; and
at least one imaging sensor package disposed on at least one substrate, wherein the at least one imaging sensor package includes at least one imaging sensor disposed on at least one imaging sensor package substrate,
wherein the at least one imaging sensor package is arranged to receive at least a portion of the light from the one or more optical elements via the at least one imaging sensor,
wherein the at least one imaging sensor package converts the received at least a portion of the light from the optical element into at least a second plurality of data signals; and
at least one circuit board, wherein the at least one circuit board is operably coupled at a selected distance above a surface of the at least one substrate of the first imaging sensor assembly and above a surface of the at least one substrate of the at least a second imaging sensor assembly,
wherein the first imaging sensor assembly and the at least the second imaging sensor assembly are separated a selected distance.

22. The array in claim 21, wherein the at least one circuit board combines the first plurality of data signals and the at least a second plurality of data signals into an aggregated data stream.

23. The array in claim 21, wherein one or more of the first imaging sensor assembly and the at least a second imaging sensor assembly further comprise:
at least one receiver package disposed on the at least one substrate, wherein the receiver package includes at least one receiver integrated circuit disposed on at least one receiver package substrate.

24. A high-speed inspection system, comprising:
an illumination source configured to generate a first beam of illumination;
a set of focusing optics configured to direct the first beam of illumination onto a surface of a sample, wherein the sample is secured on a sample stage;
at least one detector configured to detect a second beam of illumination reflected or scattered from the surface of the sample in response to at least a portion of the first beam of illumination, wherein the at least one detector includes at least one imaging sensor assembly comprising:
at least one substrate, wherein the at least one substrate includes a plurality of substrate signal lines;
at least one imaging sensor package disposed on the at least one substrate, wherein the at least one imaging sensor package includes at least one imaging sensor disposed on at least one imaging sensor package substrate;
at least one receiver package disposed on the at least one substrate, wherein the receiver package includes at least one receiver integrated circuit disposed on at least one receiver package substrate, wherein the at least one receiver package and the at least one imaging sensor package are disposed a selected distance apart on the at least one substrate; and
at least one circuit board, wherein the at least one circuit board is operably coupled at a selected distance above a surface of the at least one substrate to the at least one imaging sensor package and the at least one receiver package, wherein a plurality of data signals is transmitted between the at least one imaging sensor package and the at least one receiver package via the at least one circuit board; and a set of collection optics configured to direct the second beam of illumination reflected or scattered from the surface of the sample to the at least one detector.

25. The system in claim 24, wherein the at least one imaging sensor package is disposed on at least one interposer, wherein the at least one interposer is disposed on the at least one substrate.

26. The system in claim 24, wherein the at least one detector further comprises:
one or more optical elements configured to at least one of reflect or scatter the second beam of illumination onto the at least one imaging sensor of the at least one imaging sensor package.

* * * * *